(12) United States Patent
Ford

(10) Patent No.: US 8,489,544 B2
(45) Date of Patent: Jul. 16, 2013

(54) SYSTEM AND METHOD FOR PRIORITIZATION AND DISPLAY OF AGGREGATED DATA

(76) Inventor: John P. Ford, Unadilla, NY (US)

(*) Notice: Subject to any disclaimer, the term of this patent is extended or adjusted under 35 U.S.C. 154(b) by 1343 days.

(21) Appl. No.: 12/156,723

(22) Filed: Jun. 4, 2008

(65) Prior Publication Data

US 2009/0177045 A1 Jul. 9, 2009

Related U.S. Application Data

(60) Provisional application No. 60/933,038, filed on Jun. 4, 2007.

(51) Int. Cl.
*G06F 17/30* (2006.01)
(52) U.S. Cl.
USPC .......................... 707/602; 707/600; 707/601
(58) Field of Classification Search
CPC ................................. G06F 17/30; G06F 17/00
See application file for complete search history.

(56) References Cited

U.S. PATENT DOCUMENTS

| | | | | |
|---|---|---|---|---|
| 4,455,483 A * | 6/1984 | Schonhuber | ..................... | 705/28 |
| 5,177,796 A * | 1/1993 | Feig et al. | ..................... | 382/236 |
| 5,274,508 A * | 12/1993 | Tan et al. | ..................... | 360/48 |
| 5,303,393 A * | 4/1994 | Noreen et al. | ............... | 455/3.02 |
| 5,319,395 A * | 6/1994 | Larky et al. | ..................... | 345/605 |
| 5,321,699 A * | 6/1994 | Endoh et al. | ............. | 365/185.17 |
| 5,365,516 A * | 11/1994 | Jandrell | ......................... | 370/335 |
| 5,386,422 A * | 1/1995 | Endoh et al. | ............. | 365/185.22 |
| 5,388,074 A * | 2/1995 | Buckenmaier | ........... | 365/189.05 |
| 5,420,705 A * | 5/1995 | Ray | ................................. | 358/523 |
| 5,469,444 A * | 11/1995 | Endoh et al. | .................. | 714/722 |
| 5,481,531 A * | 1/1996 | Yamamuro | .................. | 369/47.3 |
| 5,507,024 A * | 4/1996 | Richards, Jr. | .................. | 455/260 |
| 5,526,357 A * | 6/1996 | Jandrell | ........................ | 370/346 |
| 5,585,931 A * | 12/1996 | Juri et al. | ....................... | 386/307 |
| 5,764,691 A * | 6/1998 | Hennedy et al. | .............. | 375/152 |
| 5,784,366 A * | 7/1998 | Apelewicz | ..................... | 370/342 |
| 5,805,155 A * | 9/1998 | Allibhoy et al. | .............. | 725/115 |
| 5,848,072 A * | 12/1998 | Prill et al. | ...................... | 370/471 |
| 5,877,742 A * | 3/1999 | Klink | ............................ | 345/685 |
| 5,894,494 A * | 4/1999 | Davidovici | ................... | 375/150 |
| 5,909,435 A * | 6/1999 | Apelewicz | ..................... | 370/342 |
| 5,999,562 A * | 12/1999 | Hennedy et al. | .............. | 375/152 |
| 6,072,185 A * | 6/2000 | Arai et al. | ................. | 250/492.22 |
| 6,181,609 B1 * | 1/2001 | Muraoka | .................. | 365/189.05 |
| 6,237,122 B1 * | 5/2001 | Maki | ............................. | 714/730 |
| 6,249,824 B1 * | 6/2001 | Henrichs | ........................... | 710/8 |
| 6,498,628 B2 * | 12/2002 | Iwamura | ....................... | 348/734 |
| 6,501,515 B1 * | 12/2002 | Iwamura | ....................... | 348/734 |
| 6,727,905 B1 * | 4/2004 | Narita | ............................ | 345/574 |
| 7,187,452 B2 * | 3/2007 | Jupp et al. | ..................... | 356/501 |
| 7,319,972 B2 * | 1/2008 | von Gonten et al. | ......... | 705/7.29 |

(Continued)

OTHER PUBLICATIONS

International Search Report and Written Opinion for PCT/US2009/46231, mailed on Jul. 23, 2009, 8 pages.

*Primary Examiner* — Farhan Syed
(74) *Attorney, Agent, or Firm* — Brown & Michaels, PC

(57) ABSTRACT

A computer enabled system and method aggregates data describing a particular subject. The data is then divided into a predetermined group of categories which are graphically displayed according to a predetermined pattern. Distortions in the data or anomalies in the data are made visually apparent. Associated with the display is a prioritized array of interventions recommended in response to the distortions in the data or anomalies appearing in the data.

21 Claims, 13 Drawing Sheets

U.S. PATENT DOCUMENTS

| | | | |
|---|---|---|---|
| 7,505,604 B2* | 3/2009 | Zakrzewski et al. | 382/100 |
| 7,613,352 B2* | 11/2009 | Mizuno | 382/240 |
| 7,730,967 B2* | 6/2010 | Ballantyne et al. | 175/40 |
| 7,792,375 B2* | 9/2010 | Mizuno | 382/240 |
| 7,916,960 B2* | 3/2011 | Mizuno | 382/240 |
| 2001/0042245 A1* | 11/2001 | Iwamura | 725/1 |
| 2002/0057383 A1* | 5/2002 | Iwamura | 348/734 |
| 2003/0065555 A1* | 4/2003 | von Gonten et al. | 705/10 |
| 2003/0208465 A1 | 11/2003 | Yurko et al. | |
| 2003/0236921 A1* | 12/2003 | Cordery et al. | 709/310 |
| 2004/0008219 A1 | 1/2004 | Sarel | |
| 2004/0130702 A1* | 7/2004 | Jupp et al. | 356/5.01 |
| 2005/0069207 A1* | 3/2005 | Zakrzewski et al. | 382/190 |
| 2005/0141773 A1* | 6/2005 | Mizuno | 382/239 |
| 2006/0159357 A1* | 7/2006 | Mizuno | 382/239 |
| 2006/0271421 A1 | 11/2006 | Steneker et al. | |
| 2007/0053598 A1* | 3/2007 | Mizuno | 382/240 |
| 2008/0056217 A1* | 3/2008 | Hara et al. | 370/342 |
| 2009/0177045 A1* | 7/2009 | Ford | 600/300 |
| 2009/0241027 A1* | 9/2009 | Gao | 715/704 |
| 2010/0027791 A1* | 2/2010 | Jacob | 380/210 |
| 2010/0238062 A1* | 9/2010 | Sunaga et al. | 341/176 |
| 2011/0172553 A1* | 7/2011 | John et al. | 600/544 |
| 2011/0239266 A1* | 9/2011 | Brooks | 725/146 |

* cited by examiner

Fig. 1A

PRIOR ART

PRIOR ART

Fig. 1B

PRIOR ART

PRIOR ART

Fig. 1C

△ = Na 155. Consider ICU admission and Hydration for hypernatremia and Weight loss [Dehydration]

Tumor Marker CA 27.29
3/07   30    5/07   80
Consider W/U

The unmarked anomoly (at ~ 280°)
Reflected a 6 lb weight loss occuring
After Cisplatin therapy.
Patient was rehydrated.

1. Breast Cancer 2003   Oncology Visit 2/4/08
   Current Rx Gegy 1000úg/m² Cisplatin 30úg/m² Avastin 5-15oz/log
   – every 2 wk – 8 course
   Last 1/11/08   Ca 27.29   272 (9/6/07) → 125 (12/14/07) → 121.3 (1/11/07)

2. Urine Culture + E.Coli penicillin sensitive

3. CBC
   WBC 305
   Hgb 10.4
   Plt 54

4. CMP
   Cl 109
   $CO_2$ 20

SYSTEM AND METHOD FOR PRIORITIZATION AND DISPLAY OF AGGREGATED DATA

CROSS REFERENCE TO RELATED APPLICATION

This application claims the benefit of Provisional U.S. Patent Application No. 60/933,038 filed Jun. 4, 2007.

STATEMENT REGARDING FEDERALLY FUNDED RESEARCH AND DEVELOPMENT

The invention described in this patent application was not the subject of federally sponsored research or development.

FIELD

The present invention relates to a system and method for the presentation and display of information; more particularly, the present invention relates to a computer implemented system and method which aggregates and prioritizes data relating to a particular subject to enable an observer to both identify and understand deviations or anomalies of data with respect to a predetermined base line or norm by a visual presentation of the data.

BACKGROUND

In the past twenty years there has been an explosion in the amount of information made available to professionals in all fields. The reasons for this explosion in the amount of information made available to professionals are many. Key among the reasons for the explosion in the information made available to professionals are more sophisticated and accurate testing techniques. Such sophisticated and accurate testing techniques produce numerical measurements quantifying multiple parameters. Just a few years ago, many of the numerical measurements now provided to professionals were unavailable. Because numerical measurements are easily transmitted using computer-based communication there has been a tremendous increase in the amount of numerical information provided to professionals in many fields of endeavor.

An unfortunate consequence of making large amounts of information available to professionals is that the finite capacity of human beings to absorb and to contextualize may be exceeded. When the finite capacity of a human being to absorb and contextualize information is exceeded there may be several adverse consequences. For example, important data may become buried in unimportant data. Some important data may even be inadvertently ignored. Signals of changes in data reflecting trends in the measurement of important parameters are missed. Valuable time is spent reviewing inconsequential background data. Missing key data or signals in changes in data masks the need to research the reasons for data distortions or data anomalies in key indicators.

One example illustrating the problem of exceeding the finite capacity of human beings to absorb and contextualize information is in the treatment of patients by health care providers. Health care providers, particularly medical doctors, are given complex patient reports to quickly read, properly analyze, and then, based on their analysis of the data presented, prescribe a course of patient treatment or therapy. Example of such reports appear in FIGS. 1A, 1B, and 1C. Shown therein are multiple pages of an exemplary array of medical information for a woman diagnosed with breast cancer. A busy oncologist may be called upon to review forty or fifty of such arrays of medical information each day. Despite the effort spent reviewing each chart to look for variances from a norm or to spot trends, the complex nature of a medical chart and physician (user) fatigue may cause key information, such as a variance from a norm or a data anomaly, to be missed. The consequences of missing key items of data, particularly in a health care situation, can be extremely dangerous or even fatal.

In addition to spotting a data variance from a norm, there is also a need to prioritize the information displayed to provide the professional reviewing the data with an indication of what may be the most critical of the variances from a norm and what as opposed to other variances from a norm that may be less critical. Further, if information is available regarding generally accepted interventions or therapy needed to respond to one or more variances from a norm, information regarding such generally accepted variances can be displayed.

Again, the treatment of patients by health care providers provides an illustrative example of a need in the art. Once a medical doctor reviews the report shown in FIGS. 1A, 1B, and 1C there may be a need for drug therapy intervention. If the patient has a unique condition or if the attending physician is not familiar with the use of some medications, the attending physician may have to consult a reference to select the correct medication. Thus, the need remains for a system which can quickly recognize the variance from a norm or anomaly in reported data, provide more detailed data explaining the variance from the norm or the data anomaly, and then provide a list of generally accepted drug therapy interventions. Further, such system should also be able to warn the medical doctor of any potential adverse consequences from recommended interventions such as drug interactions.

Accordingly, there remains in the art a need for a system and method which will aggregate and prioritize data relating to a particular subject. Such aggregation and prioritization of the data relating to a particular subject will enable spotting data showing either a data variance from a norm or a data anomaly. Once spotted, the user should be able to focus attention on the data variance or the data anomaly to obtain additional information about the data variance or the data anomaly. Further, there is also a need for displaying the intervention recommended, if any, in response to the variance from a norm or the anomaly. The observer of a recommended intervention should then have access to additional information further explaining the potential consequences of a recommended intervention. In addition, the observer should be able to aggregate multiple sets of data; for example, from multiple patients to enable the discovery of information characteristics of trends found in a larger universe of information revealed by observing multiple sets of data.

SUMMARY

There is provided by the system and method for data aggregation and prioritization of the present invention a solution to the problem of visually displaying the variance of data from a norm or a data anomaly to a user together with additional information which prioritizes and displays further information regarding the data variance or the data anomaly and the recommended potential interventions to be taken in response to the variances of the data from a norm or the data anomaly.

The disclosed system and method for data aggregation and prioritization of the present invention includes the use of a computer for aggregating data describing a subject, such as the health condition of a patient, and then divides the data describing the subject into a predetermined group of categories. The aggregated data is then graphically displayed initially at a predetermined position on a geometric figure, such as a predetermined coordinate point or range of points on the circumference or circle. Thus, a certain category of data will always appear at the same point or range of points. This positioning facilitates visual recognition by a user. Specifically, if a user wants to observe a certain category of data he knows exactly where to find the desired data. More particularly, all data categories have a distinct graphic address on a macro data array such as coordinate on a circulator array much like the directional positions on a compass. Distortions and anomalies in the data are graphically shown in an easy-to-read figure as variations from a norm or a data anomaly.

The display created by the computer is designed to create a visual macro indication of the data describing the subject including a visual indication of the existence of data falling above or below a predetermined norm. The computer created display provides a link to a micro display of the data using the visual indication of the data describing the subject falling above or below the predetermined criteria. The micro display further describes the data identified on the macro display of the data describing the subject. The displays of sets of data provided by the system and method of the present invention may be aggregated to enable to the discovery of information characteristics and trends found in a larger universe of information revealed by observing multiple sets of data.

Also associated with the display of data is a display of the history of interventions previously made along with additional information describing recommended interventions according to a predetermined priority. More particularly, the disclosed system and method provides a layering of data starting with a macro data array such as a data array on a circle. The next layer of data display provides greater detail; for example, the data in one quadrant or one accurate sector of the initial circular display. This display may include a feature by which the user demonstrates and records an acknowledgment of having observed certain key portions of the data. Another layer of data display provides an historical or time-expanded display of the parameters shown in data display having more detail such as the quadrant of the initial circular display.

DESCRIPTION OF THE DRAWING FIGURES

A still better understanding of the system and method for data aggregation and prioritization of the present invention may be had by reference to the drawing figures wherein:

FIGS. 1A, 1B, and 1C are examples of prior art paper reports of information reporting the health condition of a patient with restaging breast cancer and the various types of medical care being provided to the patient;

FIG. 4 is a screen image of an expanded display of data showing both an acknowledgment of the observation of certain data and other data displayed in an historical context.

DESCRIPTION OF THE EMBODIMENTS

Figure 2A:
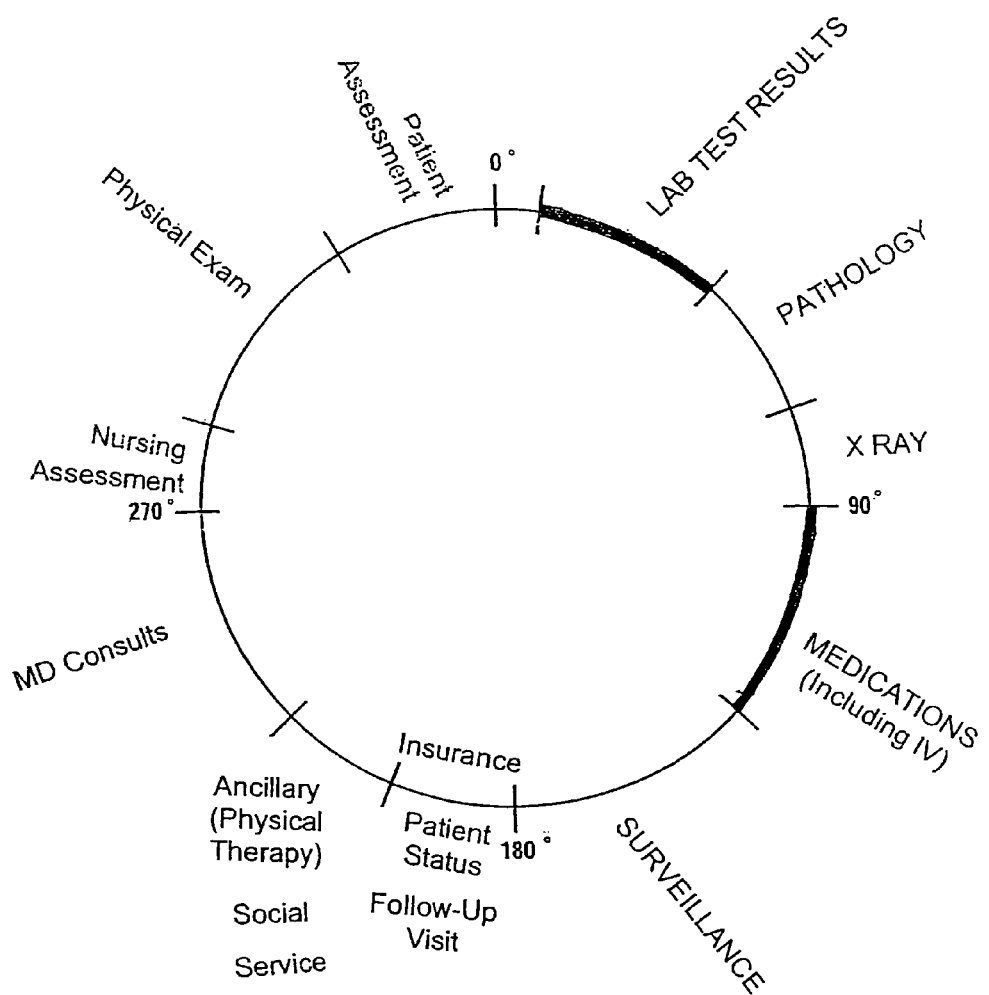
FIG. 2A is a screen shot of an exemplary substantially circular geometric figure around which has been arrayed various types of information relating to the health condition of a patient and the medical care being provided to the patient.

As explained in the BACKGROUND and SUMMARY portions above, professionals in numerous fields are provided with multiple reports including data reporting measurements or test results including numerous parameters. The data in the reports may be used to represent the condition of a particular parameter along with a history of the work done or interventions made by others. The professional evaluating the reports is then expected to use professional judgment to determine if the data warrants intervention or if a future course of action is necessary before an intervention is made.

In most cases, the judgment of a professional is needed because the data reporting measurements or test results including of one or more parameters show what may be called baseline data and other data that may be called intervention data. Baseline data typically expresses or confirms test results within a normal or anticipated range of values. Intervention data is that data which shows a deviation of data from a norm or possibly a data anomaly. If a data deviation from a norm or a data anomaly is shown some type of intervention may be needed to address the deviation of data from a norm or the data anomaly. Proper intervention may be a prescribed course of action or alternatively proper intervention may be verifying test data particularly when there is on unpredicted or unusual data anomaly. In other cases, the data reporting measurements of one or more parameters may be indicative of a trend for which intervention may or may not be needed; however, the trend may be indicative of a potential for some other situation recognizable by the professional as requiring additional testing or more frequent testing.

Those professionals called upon to exercise professional judgment must determine if deviation of data from a norm or a data anomaly represents a situation in which known interventions will provide predictable results. Many of such interventions are generally accepted by professionals; however, other some less well known situations may require research or further study on the part of a professional. Still other interventions may trigger unanticipated complications which could exacerbate a measured condition.

Detracting from the ability of a professional to exercise professional judgment are two key factors. The first factor, as explained in the BACKGROUND portion, is the finite ability of a human being to absorb and contextualize data Herein, the professional is presented with so much information that important deviations from a norm or anomalies in test result data are potentially masked by being buried in other test result data.

The second factor detracting from the ability of a professional to exercise professional judgment is that the judgment of a professional is only as good as the recall of the professional with regard to current thinking about the proper response to certain test results. For frequently occurring conditions, the professional may be able to provide a rapid recommendation for an intervention or for a course of action to be taken. For infrequently occurring conditions, the professional may need to do some research to determine what others in the field have recommended as a response to a similar situation or the most current thinking regarding the implications of a recommended response.

Professionals faced with complex situations rarely find one piece of data or one bit of information which represents a data deviation from a norm, a data anomaly or both. Accordingly, additional professional judgment is required to determine which data deviation from a norm or which data anomaly is the most important in terms of the need for an intervention. While the judgment of a professional will be determinative in assessing the priorities for intervention, the size of a deviation from a norm or the criticality of a data anomaly may be determinative in establishing priorities. In other cases, the judgments of other professionals about the priorities for intervention may be helpful to a professional when determining the need for one or more intervention steps.

By use of the foregoing general description of the activities of a professional when rendering judgments about needed intervention suggested by the data from measurements or test reports and the history of a particular situation, the system and method for data aggregation and prioritization of the present invention will be described. To place the description of the present invention in a more practical context, the following description of the embodiments illustrates the operability of the disclosed system and method for data aggregation and prioritization in a health care context.

Figure 1A:
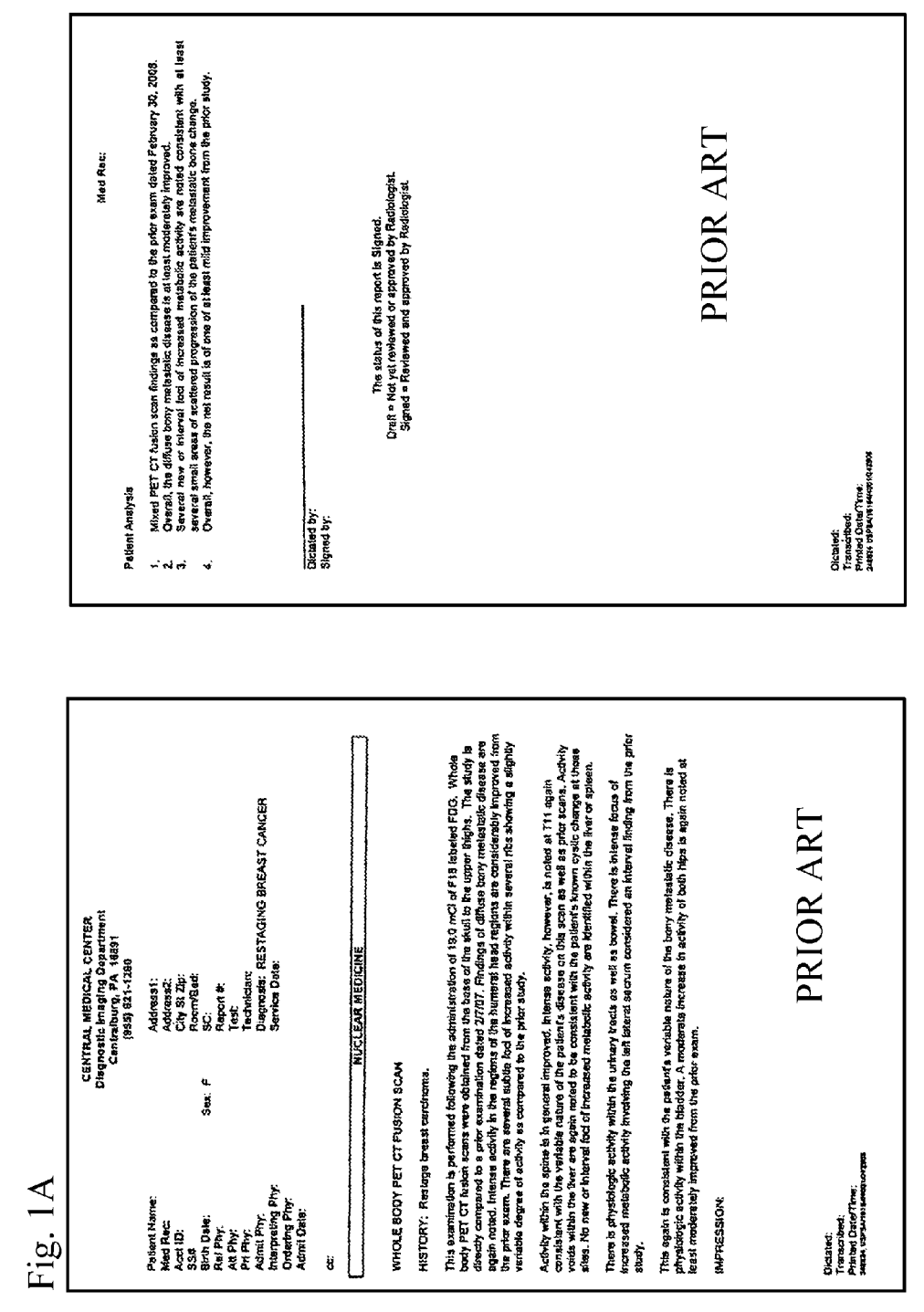
Figure 1B:
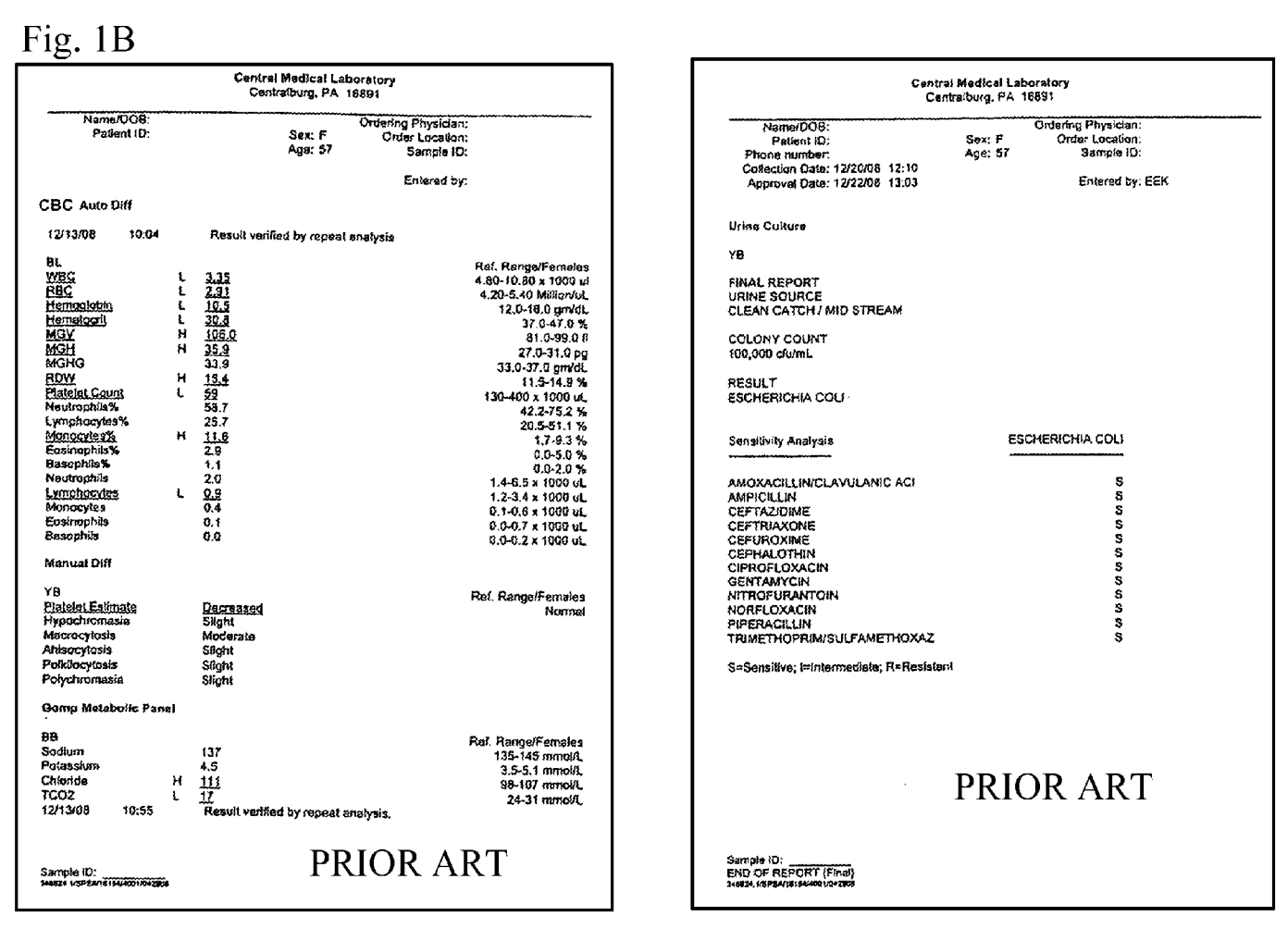
Figure 1C:
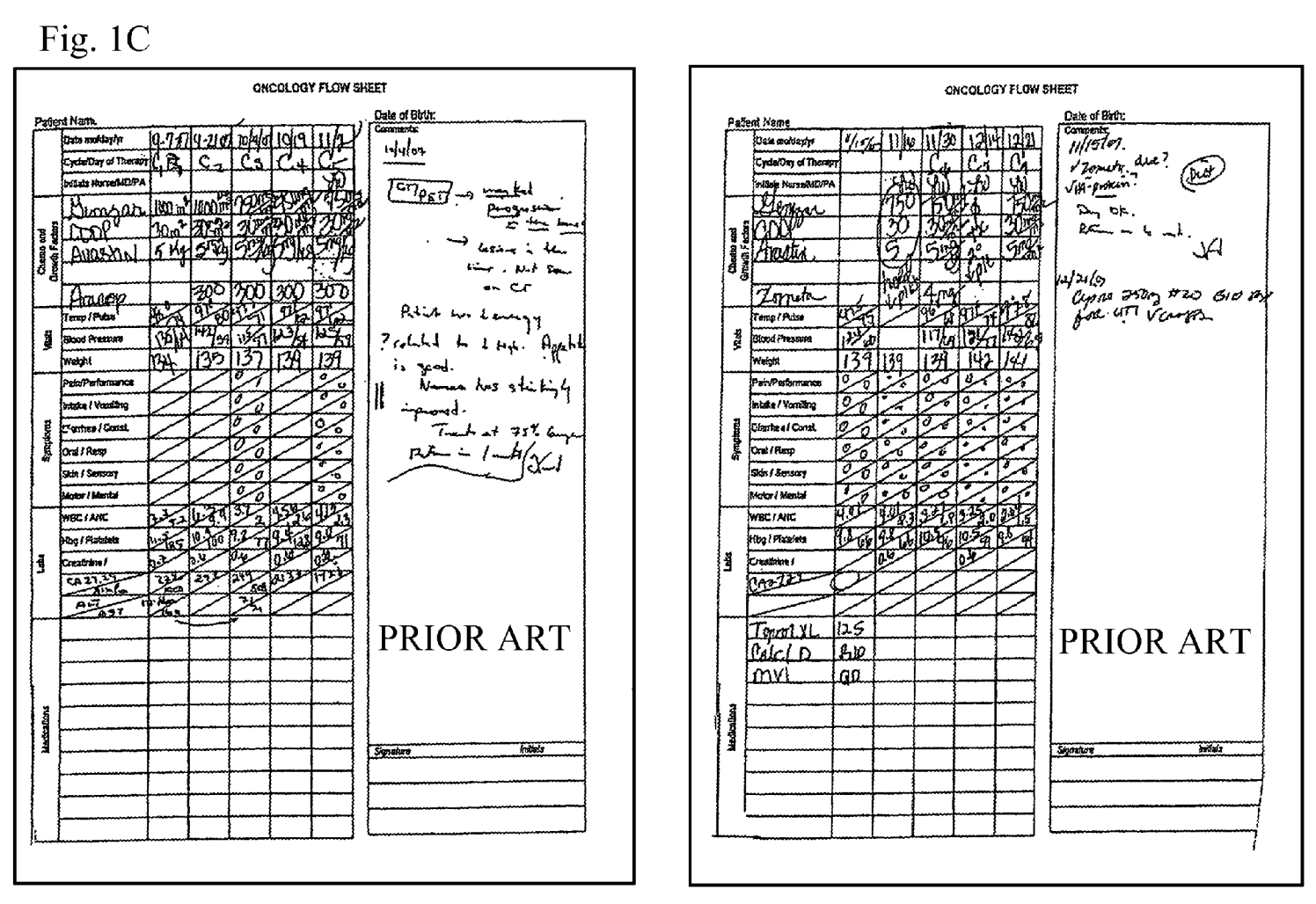

When treating a patient, a medical professional, more particularly a physician, is presented with information and history about a patient in various forms. One prior art example is shown in FIGS. 1A, 1B, and 1C. Much of the data presented to a physician, is in the form of numbers produced by direct measurement or lab tests. While laboratories providing measurements or test results may often indicate if a particular measurement or test result is outside of a predetermined range, the out of range measurement or test result may easily be misread or completely overlooked when a physician has only a short period of time to review numerous complex reports listing the results of various measurements and tests; for example blood tests, urine tests, etc.

Those of ordinary skill in the art will understand that the following exemplary embodiment in the health care context is illustrative and that the system and method of the present invention may be used in any situation where information is presented to a professional for the exercise of professional judgment regarding any actions or interventions to be taken or not taken.

According to a basic embodiment of the system and method of the present invention data typically reported on the health condition of a patient is arrayed as shown in FIG. 2A. Therein, a circle is shown as being exemplary of a graphic representation of what the system and method of the present invention presents to a user. In other situations, other one-dimensional shapes such as a line may be used. Alternatively, a two-dimensional shape such as an oval, a triangle, or a rectangle, etc. may be used without departing from the scope of the present invention. In yet other situations, a rotatable two-dimensional representation of a three-dimensional object as is found in CAD drawings may be used. The circumference of the circle or the perimeter of the selected figure indicates a normal condition. If a normal condition can exist over a range of numbers, portions of the circumference of the circle may be a thickened line as shown in FIG. 2A. The circle is chosen for the exemplary embodiment because positions around a circle are easily described by coordinates. Each specific type of data will have its own specific co-ordinate. Such positioning enables a user to quickly identify, in terms of location of the circle, the type of data that is anomalous and this is shown as a radial line or ray extending above or below the circle.

Surrounding the circle shown in FIG. 2A is a predetermined array of information categories. Specifically, proceeding clockwise around the circle, the first approximately 45° arc is for the display of lab test results. Next is an approximate 30° arc for showing pathology test results. Completing the first 90° of the circle is another small arc on which information regarding x-rays is displayed. Proceeding further around the circle along the next approximately 45° arc are those medications being administered to a patient. The medication arc is followed by a surveillance arc of approximately 45°. Shown in the surveillance arc will be such activities as a vaccination or a mammogram.

The next approximately 90° arc moving upward from the bottom or 180° degree position of the circle is a patient history sector to include the patient status and such things as physical therapy, work by social service agencies, and consultations with other physicians. The last 90° arc proceeding to the top of the circle from the 270° degree position is for patient assessments to include a nursing assessment, a physical exam, and an overall patient assessment. Key to the utility of the diagram shown in FIG. 2A is that the same information appears at the same location on the circular display of measurements or test results for every patient. After a short period of use, the physician using the system and method of the present invention will be able to focus in on the needed information describing the health condition of a patient without the need for the display identifying labels positioned around the circle. Thus, for simplicity and for ease of viewing the label portion of the screen shown in FIG. 2A, the identifying labels may be shut off or used only as needed for training or verification purposes.

The array of medical information graphically representing test results as shown in FIG. 2A is suggestive only to illustrate the operability of the system and method of the present invention. The greatest utility of the disclosed system and method would be obtained if a medical care improvement agency, for example, a medical practice specialty board were to standardize the format for the graphical array health of care information in a particular practice area such as internal medicine, surgery, urologists, etc.

Figure 2B:
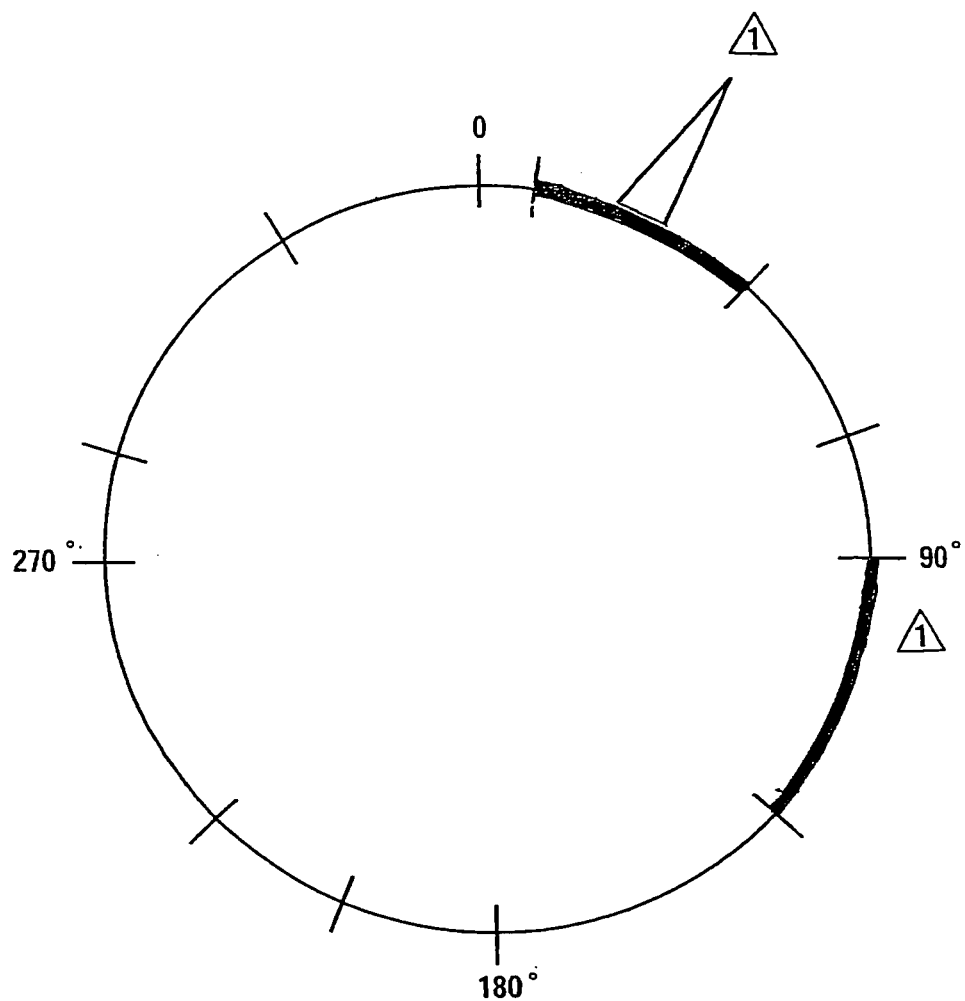
FIGS. 2B, 2C, 2D, 2E and 2F are screen images of a basic embodiment of the present invention graphically presenting individual test report deviations from a norm along with an explanatory note further describing the individual test report deviation from a norm or suggesting a potential intervention.

FIG. 2B is illustrative of the first screen in a basic embodiment of the present invention where a single deviation from the norm showing an abnormal condition or a data anomaly is shown. This deviation of data from the norm or the data anomaly is shown by the numeral "1" in a triangle. Note by comparison to FIG. 2A that numeral "1" in a triangle appears in two sectors; one relating to lab test results and the other sector relating to medications. The explanatory note at the bottom of the screen indicates that the reason for the appearance of the "1" in a triangle is because the test result about the presence of sodium (Na) is abnormal; that is the reported amount of sodium (Na) is outside of normal range or above a norm. The relationship of this deviation from a normal range is reflected by the height of the triangle including the number "1" from the parameter of the circle at about the 20° location. In the note at the bottom of the screen image, a suggestion is made that an intervention described as "Consider IV Hydration" is recommended as a therapy in response to the test result illustrating data describing the patient's high sodium condition.

Figure 2C:
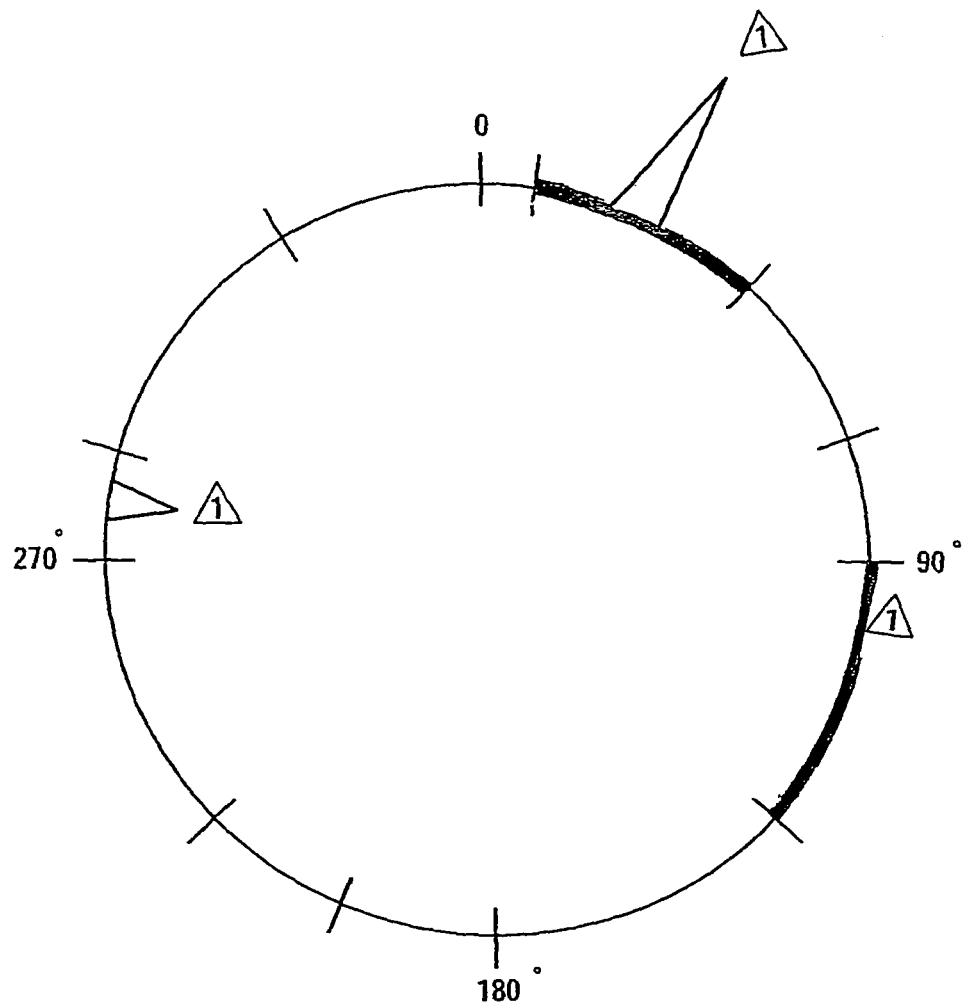

A similar situation is shown in FIG. 2C. Note here that the level of sodium sensed is much higher as shown by the greater distance of the numeral "1" in a triangle at about the 10° location. Note also that a second and third numeral "1" in a circle appears at the 90° position and just above the 270° position in those portions of the circle identified, according to FIG. 2A as being for medications and the reporting of physical exam information respectively. As indicated in the note positioned just under the circle, the sodium level test result is reported as being 155. A sodium test result of 155 indicates a critical condition thus triggering a message recommending the admission of the patient to an ICU as well as hydration for the treatment of hypernatremia and weight loss.

Figure 2D:
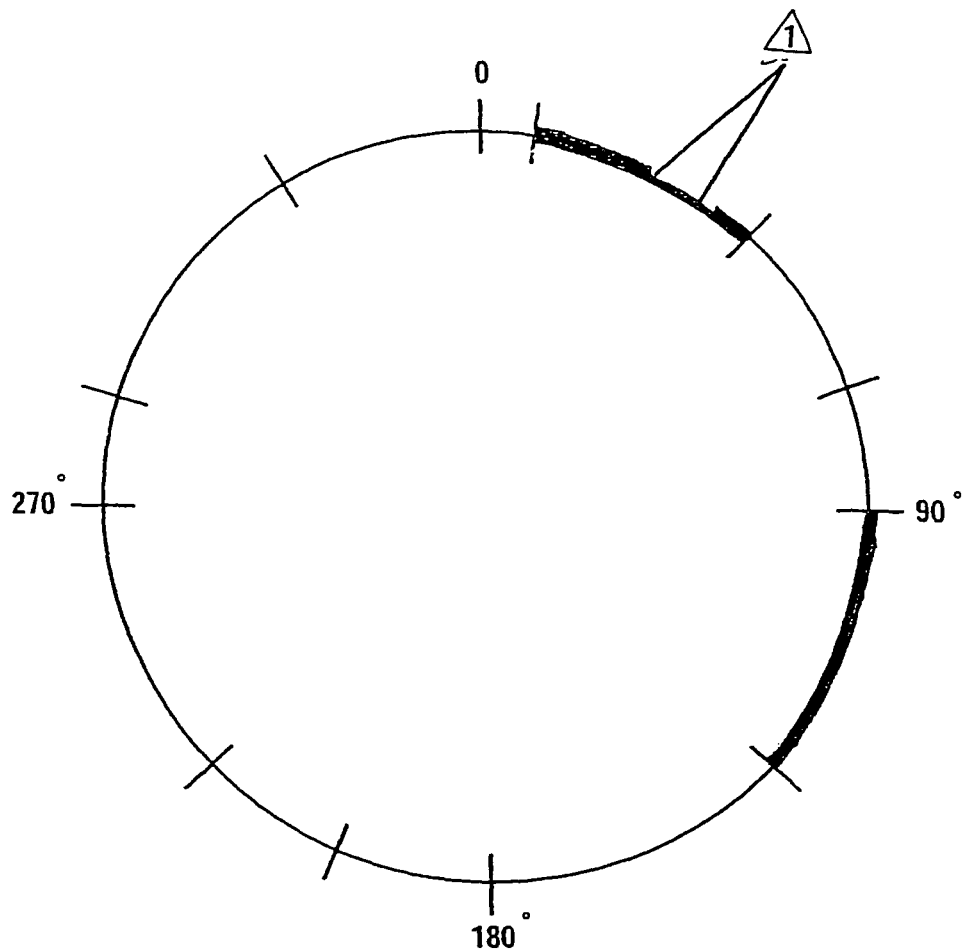
Figure 2D:
Figure 2E:
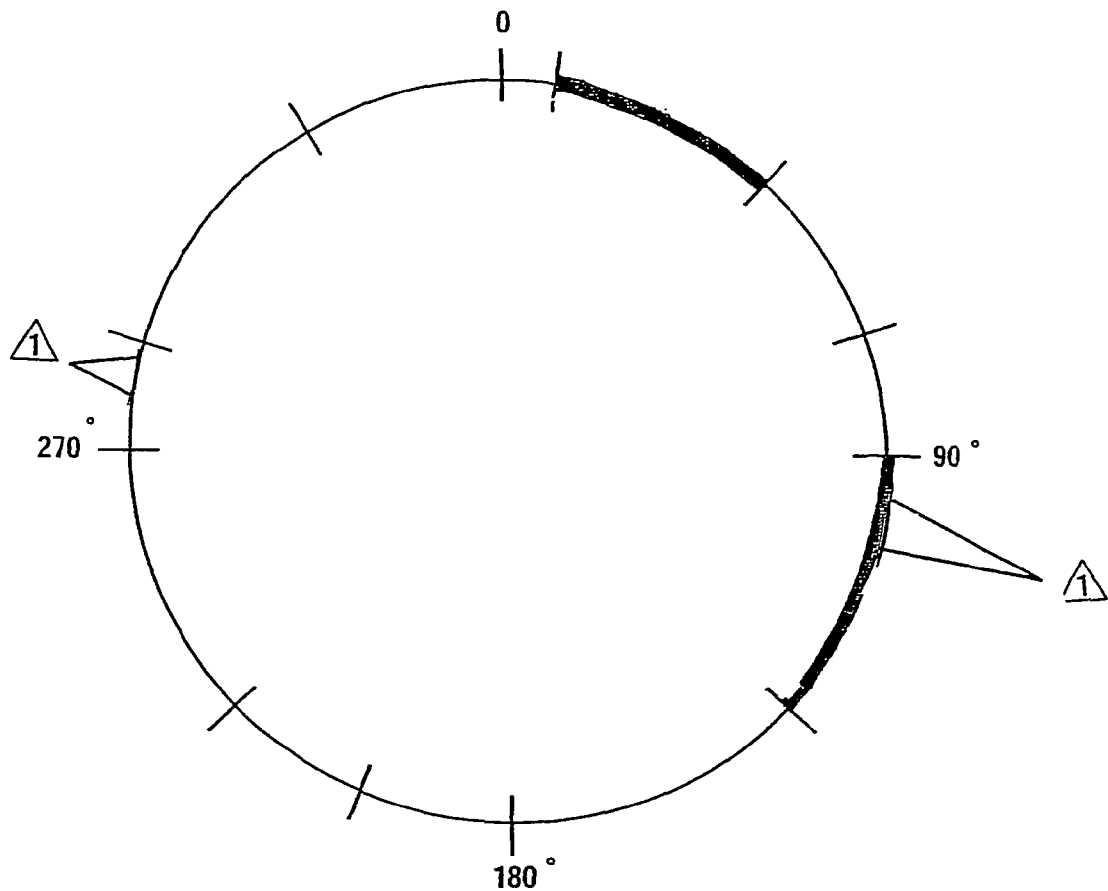

Yet another situation is shown in FIG. 2D. Herein, the presence of the numeral "1" in a triangle indicates that a pathology report has produced a number reporting a test result that is out of a normal range for a tumor marker test result. Specifically, the tumor marker is Ca 27. 29. Also reported is the fact that the tumor marker test result was 30 on March 2004 and 80 on May 2007. The physician may need to alter therapy or consider a work-up (W/U) such as a biopsy Still another situation is shown in FIG. 2E. The circle shown in screen in FIG. 2E shows a "1" in a triangle indicating that there is a deviation of data from a norm or a data anomaly in the medication portion of the circle just below the 90° marker and in the nursing assessment portion of the circle just above the 270° marker. These two indicators are explained in the accompanying note wherein the observer is warned that patient is allergic to penicillin but, for some reason, is being administered doses of penicillin.

Figure 2F:
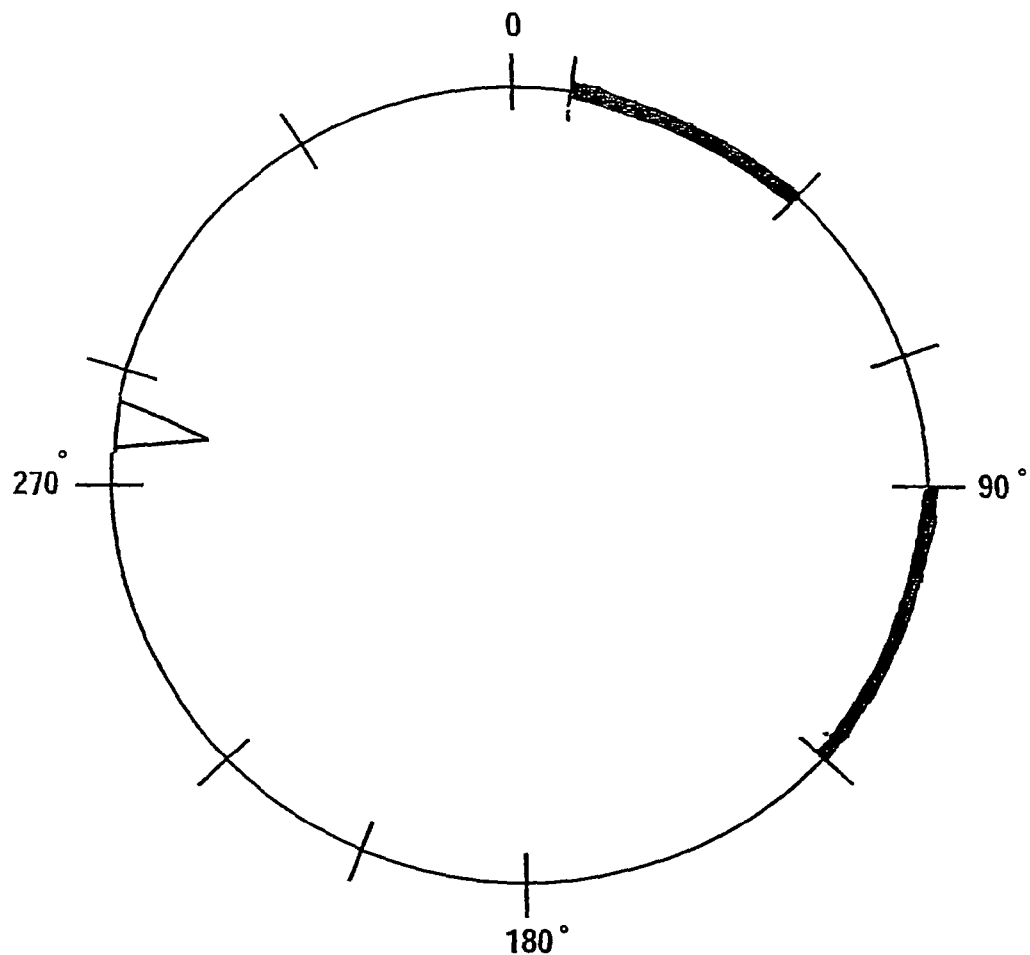

FIG. 2F shows an anomaly at approximately the 280° position by a small triangular projection jutting into the circle showing that the reported data is below the predetermined norm. The nursing assessment is reported in a note under the circle indicating a 6 lb weight loss after the administration of Cisplatin therapy to the patient. Further indication in the note reveals that the patient was re-hydrated.

Figure 3A:
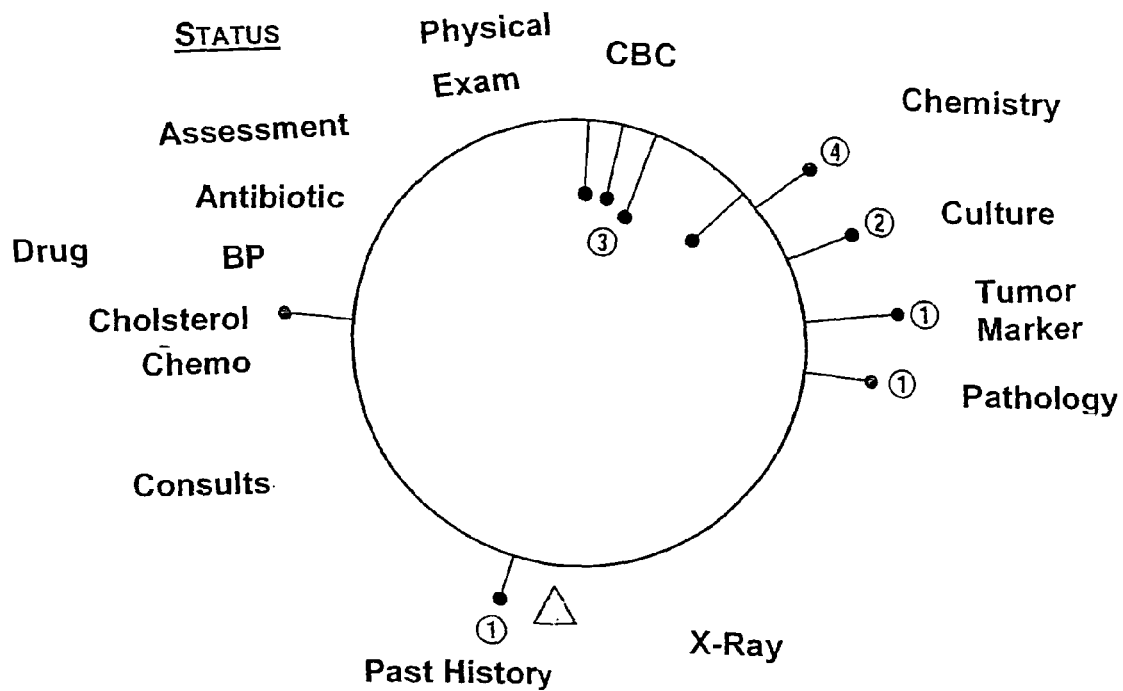
FIG. 3A is a screen image of an advanced embodiment of the present invention graphically presenting multiple deviations from a norm along with an explanatory legend identifying the data displayed at a predetermined location on the circular display.

A more advanced embodiment of the disclosed system and method appears in FIGS. 3A, 3B 4A, 4B and 4C. Herein multiple test results are displayed around a substantially circular shape. Radial lines or rays extending outwardly from the circle indicate a measurement or a test result above a predetermined norm. Radial lines or rays extending inwardly from the circle indicate a measurement of a test result below a predetermined norm. The length of the radial line or ray is a function, for numeric data, of its statistical confidence limits. For example, data that is one standard deviation norm would be, rendered as a line of a pre-determined length. Data that is two standard deviations away from a norm would be shown as a longer line, and so on. Shown below the circular display of data is a box of icons associated with this exemplary screen display. In FIG. 3A the LEGEND icon has been selected to produce an array of labels identifying the information displayed at various locations around the circle.

In FIG. 3A a circle is displayed along with the needed labels to determine the various information displayed at various portions of the circle for an oncologist. One of ordinary skill in the art will understand that physicians practicing in certain specialty areas such as internal medicine, surgery, or urology may desire a custom set of labels pointing them to the information deemed to be most critical. In yet other situations individual physicians may further desired a unique set of labels. It is also possible to create an array of general data useful to physicians irrespective of specialty or useful to nursing staff.

Beginning at the top of the circle shown in FIG. 3A is an indication of CBC. Next is an arcuate sector covering about 45° in which information dealing with Chemistry is reported. The Chemistry sector is followed by several smaller arcuate sectors describing information about Cultures, Tumor Markers and Pathology. At the bottom of the circle more subjective information is shown such as the analysis of x-rays, past history of the patient and consultation reports from other physicians. In the upper quadrant of the circle on the left side appears information about treatment. Shown are arcuate sectors for information relating to Chemotherapy, Cholesterol treatment, Blood Pressure, Antibiotics, Assessment and Physical Exams.

Shown at the bottom of a circle in FIG. 3A is a small triangle. The location and the appearance of this small triangle symbol in the illustrated embodiment is an indication of the need for intervention regarding a particular observation. Thus, a quick scan of the circle by a physician for the appearance of a small triangle will quickly alert the physician that a comparison of a test result or a portion of treatment history has been made and that some intervention may be called for. The distance of the position of the small triangle from the circle is indicative of the length of time to the next appointment with a physician. If desired, the small triangle may be colored with an attention-getting color or be made to flash.

Figure 3B:
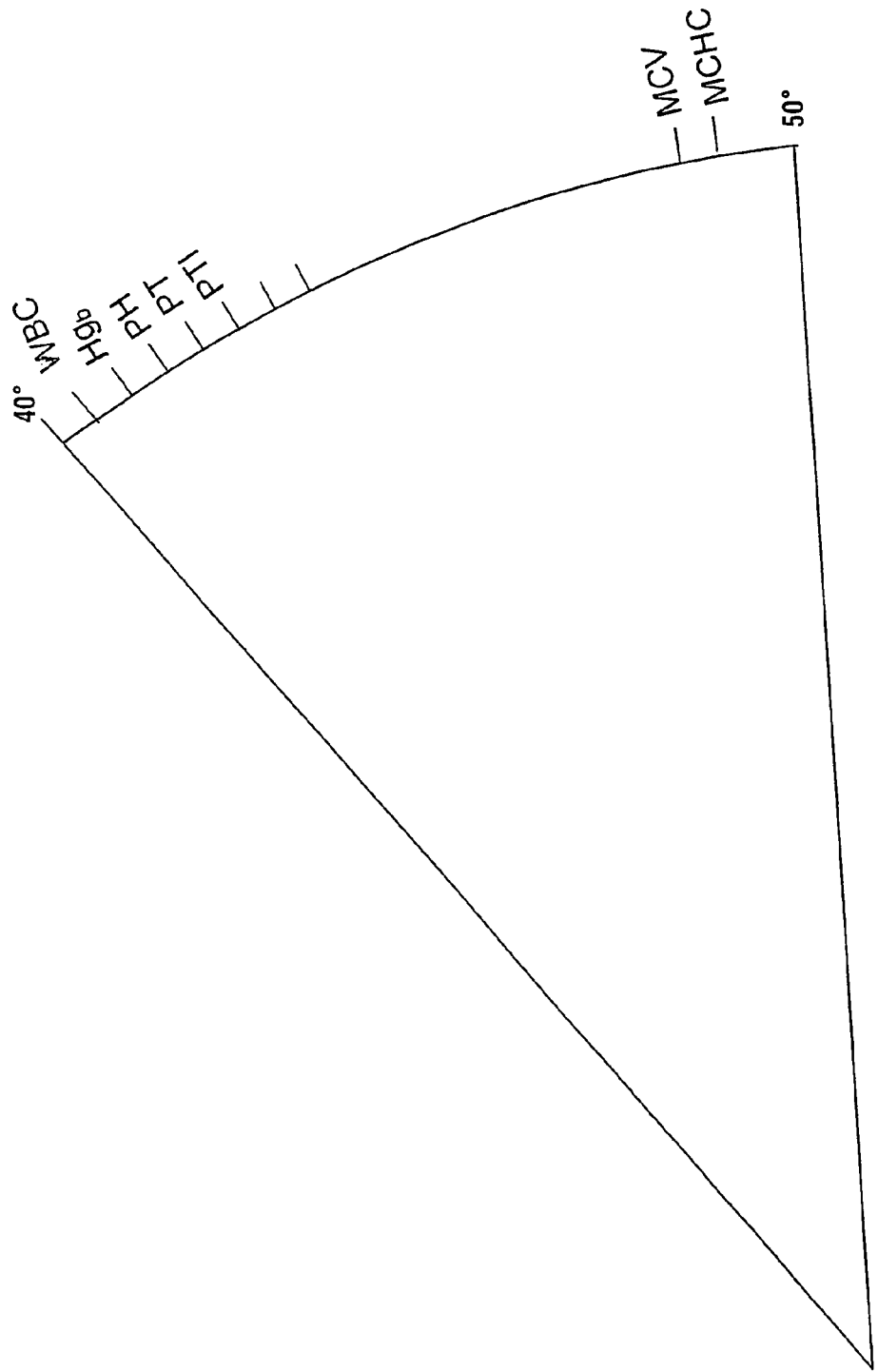
FIG. 3B is a screen image of an enlarged sector of the circle shown in FIG. 3A with an expanded legend identifying additional data.

Of particular concern to this physician viewing the display of information shown in FIG. 3A is the Chemistry section. Accordingly, the physician can click on this sector of the circular array of information or highlight this sector and click on REVIEW icon (not shown) to obtain additional details. The additional details are shown in FIG. 3B along with additional labels obtained by using the icon identified as EXPANDED LEGEND. As may be seen in FIG. 3B is an enlarged approximate 10° arcuate sector, specifically that arcuate sector which extends from about 40° to about 50° of the circle shown in FIG. 3A. Herein a broader array of test results is shown as radial lines extending outwardly from the arcuate portion of the sector. As with FIG. 3A, a long radial line extending from the arcuate portion of the sector will indicate a significant deviation from a norm or a data anomaly. While not shown, it is also possible to add further explanatory notes along with the sector shown in FIG. 3B.

Figure 4A:
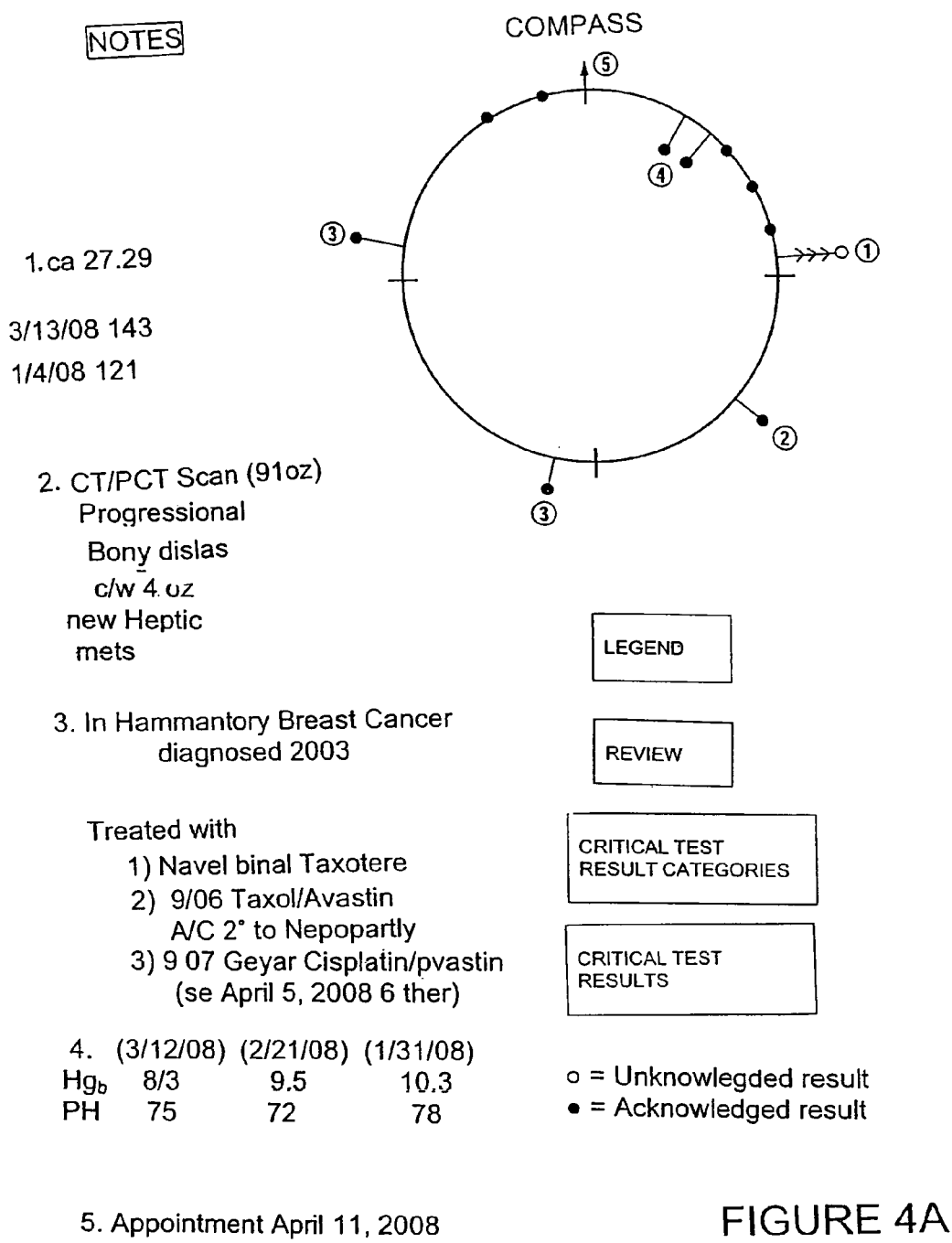
FIG. 4A is a screen image of the advanced embodiment of the present invention graphically presenting multiple deviations from a norm along with explanatory notes to assure recognition of the deviations by an attending physician.
Figure 4B:
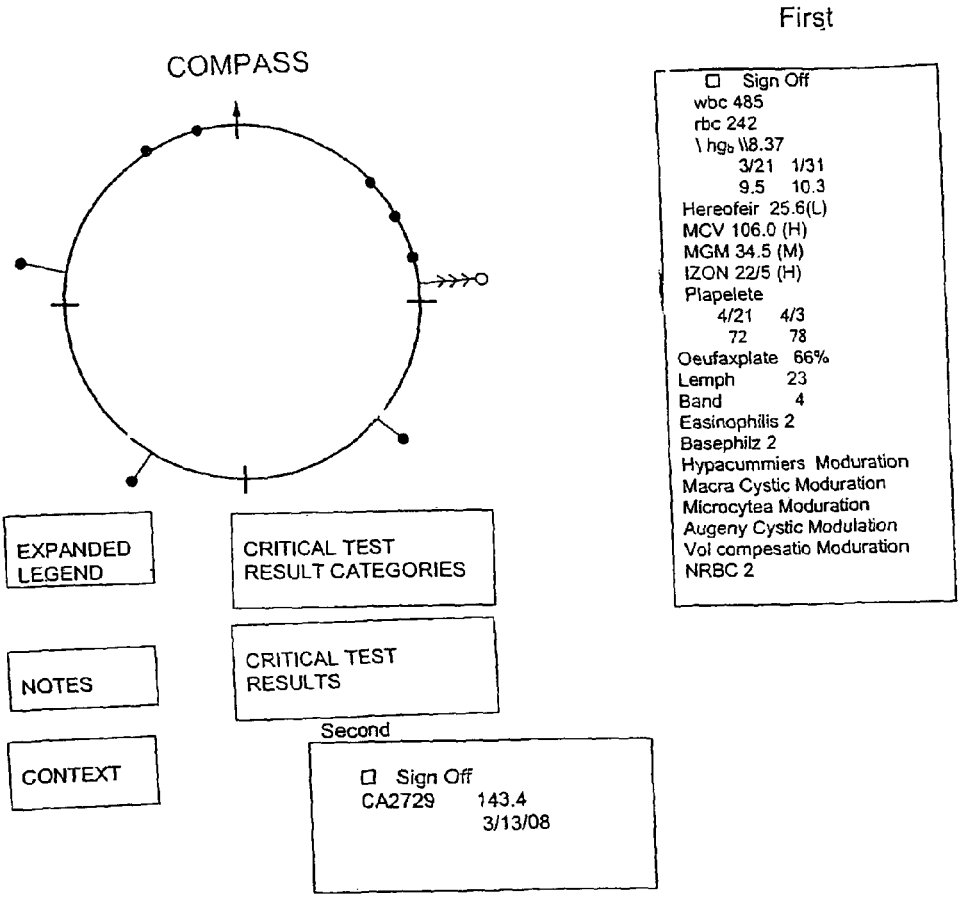
FIG. 4B is a screen image of an expanded display of data requiring an acknowledgement of the observation of certain data deviating from a norm.
Figure 4B:
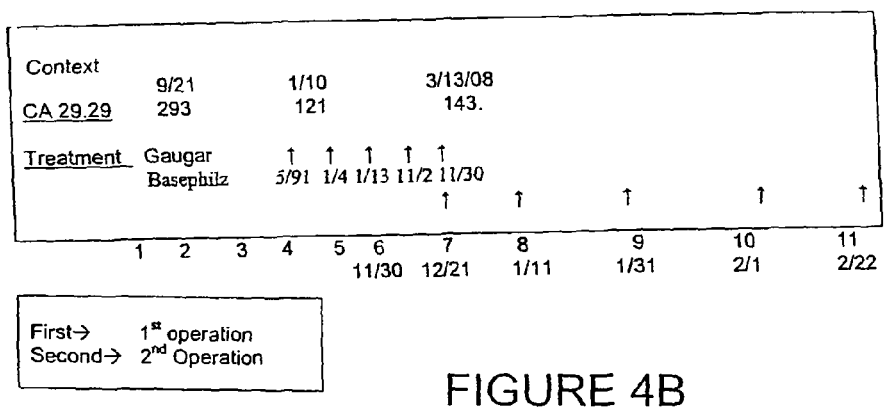

As shown in FIG. 4B a physician may obtain notes under the circle by selecting the NOTES icon Herein, by selecting the NOTES icon the patient has been diagnosed with breast cancer. Hence, the array of information displayed around the circle relates to those categories of information that an oncologist, particularly an oncologist specializing in the treatment of breast cancer, may want to see.

Also shown in FIG. 4A is yet a more advanced preferred embodiment of the present invention. Once again notes appear on the screen along with circular array of information. As in the prior embodiments the notes are keyed to numbers appearing near the radial lines or rays extending outwardly from the circle. Some of the circles at the end of the radial lines are filled in and some are not. As explained above, a circle which is not filled in indicates that the information has not yet been reviewed by the physician observing the screen shown in FIG. 4A. A filled in circle shows that the information has been reviewed and acknowledged by the physician. The screen shown in FIG. 4A adds yet another visual indicator not shown in the embodiments described above. This visual indicator is a series of arrows along the radial line or ray at the approximate 90° position near the circle including the numeral 1 on the right side of the circle. This series of arrows indicates an upward trend in a test result over time. Additional indicators may include different types of highlighting such as a flashing word or symbol for different test results or tests results above a predetermined level. Such indicators may include colors such as red for severe abnormal indications, amber or yellow for non-severe abnormal indications or green for abnormal indications that bear watching or have been noted by others as worthy of future attention. Potentially lethal indications may include a skull and crossbones symbol.

As in the examples of the basic embodiment shown in FIGS. 2A, 2B, 2C, 2D, 2E and 2F, in FIG. 4A explanatory notes appear under the circle. The multiple notes shown in FIG. 4A correspond to the numbers on the radial lines extending either outwardly from or inwardly into the circle. The explanatory notes provide two functions. First, the order in which the explanatory notes indicates a suggested priority of the need for multiple responses to intervention-indicated data. For example, the order of the explanatory notes may correspond to the size of the deviation of the data from a norm. As shown in Note 1, the small triangle, explained above as indicating a need for intervention, is further described as showing an appointment with an oncologist on Apr. 11, 2008. Other entries in the Notes indicate the diagnosis of breast cancer in 2003 and the current array of medications being taken by the patient in Note 5. Yet other notes may inform the user that a measurement or test result is so far out of range that it must be a true data anomaly.

The entries in Note 4 relate back to the history of a patient's blood test. Most notable are the changes in Hgb and in the Platelet count which contextualizes this important information.

As indicated above, some of the circles which appear in FIG. 4A are open and some are filled in. When a physician decides to look closer at the information associated with an open circle, such analysis may be accomplished by placing a mouse-movable pointer over the open circle. A display of information as shown in FIG. 4B appears to indicate the review of the information presented in FIG. 4B, the physician will be asked to click on an icon positioned above the more detailed information labeled SIGN-OFF. Clicking on the SIGN-OFF icon is an indication that the physician has observed and considered the identified information and will cause the open circle appearing in FIG. 4A to be filled in. Information worthy of particular attention may be highlighted by the presence of an arrow.

In FIG. 4B is the array of information requiring observation and a recognition of acknowledgement in a SIGN OFF box. The information in the sign off box is shown because of its deviation from a norm. Checking the box near the words SIGN OFF will provide an indication that the physician has observed and acknowledged the data displayed. No further operations with the disclosed system are possible until the SIGN OFF box has been checked. As indicated above, once the SIGN OFF box has been checked, the open circles in FIG. 4A will be filled in.

In FIG. 4C another SIGN OFF box appears requiring acknowledgement by the user. Once observation of this data has been acknowledged the user by clicking the box next to the words SIGN OFF, the user may proceed onto a CONTEXT box to display a more detailed patient history as shown along the bottom of the screen image.

A still better understanding of the disclosed system and method may be had by a description of the various icons shown above, as follows.

The LEGEND icon provides a command to the computer to display the identifying information as shown in FIG. 2A and in FIG. 3A wherein labels of tests result categories are added to describe the information to be displayed at a predetermined location. For the new user, use of the LEGEND icon provides a quick indication of where information of interest appears. No numbers or test results are shown. Another command or a click on the LEGEND icon as shown in FIGS. 2A and 3A causes the labels to disappear as shown in FIG. 4A.

The EXPANDED LEGEND icon provides a command given to the computer to obtain more detailed information associated with an enlarged display of an arcuate sector. An example of such detailed information appears in FIG. 3B. After the EXPANDED LEGEND icon is selected and the micro display of available information is revealed, the user may still click on a designated information identifier to achieve yet more information about a particular measurement.

The NOTES icon provides a command which displays the explanatory notes which appear near the macro information display as shown in FIG. 4A where data is displayed which deviates from a norm or is a data anomaly. Selecting the "NOTES" icon will make the notes appear or disappear. Each of the numeric identifiers is keyed to written descriptions at the bottom of the screen. As previously indicated the set of notes is organized so that the highest priority or most deviant or abnormal measurement or test result information appears in the first note. If desired, the displayed notes may be grouped into one or more categories to characterize the criticality of the information displayed.

The specific entries associated with each note include the value of a test result along with any recommended intervention or available historical data putting the test result in a context where it is best understood. As explained below, the information displayed in the notes is the same as the information that may be obtained when an icon identified as "CONTEXT" is selected as shown in FIG. 4C.

The icon labeled NOTES enables the position of the text of the notes to be displayed when it is most readable for the user. A second selection of the NOTES icon will cause the explanatory notes to disappear.

If desired the screen treatment the explanatory notes can be printed out and added to the paper portions of a patient's treatment record. Also if desired, the indication on the screen may be forwarded to another computer at a distant location for consultation with another health care professional. Alternatively, a doctor visiting a hospital away from where his/her patients are located may monitor a patient's condition or the progress of intervention therapy at the doctor's home hospital. In still other situations the information on the screen may be forwarded to a records storage facility or to a provider of medical insurance. While the only limit to the number of notes presented is the size of the screen, 5-10 notes per patient is satisfactory. If the condition of a patient changes, additional notes may be added and the numbering of the notes to indicate their priority will be changed.

If a physician wants to take another look at a set of test results, the mouse-movable icon is moved as described above to an area of interest on the macro display of information shown in FIG. 4A to obtain an expanded display as appears in FIG. 3B.

While a routine set of labels for the arcuate sectors of the circle appears as shown in FIG. 2A and in FIG. 3A, CRITICAL TEST RESULT CATEGORIES may be selected to display those categories of test results which could have a very rapid adverse health consequences for a patient. More particularly, the CRITICAL TEST RESULT CATEGORIES are established to provide a way for the physician (or his surrogate within a hospital or within a laboratory to determine Such CRITICAL TEST RESULT CATEGORIES may be standardized for a specialty practice area, a hospital, or set up according to the preferences of an individual physician. When the CRITICAL TEST RESULT CATEGORIES icon is selected, only test results in these categories are displayed as open circles, as shown in FIG. 4A, attached to a radial line. As indicated above, acknowledgement of the observation of a measurement or a test result by the selection of an icon labeled SIGN-OFF icon is needed to fill in each open circle. Those test results which are critical but are readily expressed numerically appear as radial lines extending outwardly from the circular array of information.

As indicated above, a custom set of "CRITICAL TEST RESULTS" may be selected by the user. Further, the user may determine at what level a measurement or a test result is determined to be abnormal or an anomaly. This customizing feature can be adopted to multiple types of practices and even to the preferences of individual practitioners. Selecting a customized set of CRITICAL TEST RESULTS will display those test results best displayed as a numerical value. When selected, the information shown will be deviations from the 95% confidence limits of either the population at large or whatever confidence level is selected with respect to a data set. Values above the confidence limits appear as radial lines extending outwardly from the circle and values below the confidence litmus appear as radial lines extending into the space within the circle. Once again the open circle and filled circle system described above is exemplary of a method used to determine if certain items of data have been observed. Further, and as indicated above, the radial line extending to the circle may include arrow markings indicating a decreasing trend, an increasing trend or stability.

As shown in FIG. 4C, a "CONTEXT" icon may be available to enable a physician to obtain a history of measurements or a chronology of test results. Further information made available may be a history of the test type and previous interventions made. Such interventions may include medications administered orally or by IV.

Those of ordinary skill in the art will understand that displays of information as shown in FIG. 4A may be laid one over another to note changes in the test results of a particular patient or the characteristics of a patient population. When displays of information from multiple patients are laid one over another particular trends such as high levels of a particular substance in patients such as a pollutant found in a selected geographic area or the effectiveness of a particular health care facility in treating a medical condition may be identified. Such displays of aggregated information from multiple patients will enable physicians or bio-statisticians to identify situations where significant data exists such as at the tail of a normal data distribution for further investigation.

A further utility provided by the disclosed system and method is the assembly of predetermined sub-sets or strings of data such as shown in FIG. 3B. Such sub-sets or strings of data may be displayed on a two-dimensional array or on a rotatable two-dimensional representation of a three-dimensional object as found in CAD drawings. The use of such utility may be particularly helpful in some forms of data mining or forensic analysis whose seemingly unrelated sets of data are compared to determine heretofore unfound similarities or relationships among certain conditions reported by measurements or test results.

By aggregating sets of data constructed as described in the preceding paragraph such as by laying multiple images one-over-the-other, certain characteristics of a universe may be determined such as if data which seems to appear at the tails of a normal distribution may signal a heretofore unrecognized condition.

By use of the disclosed system and method users will be able to rapidly and consistently identify changes in data representing a particular measurement or test result. Once identified the changes in the measurement or test result will be supported by access to a prioritized subset of vital information providing both additional information and recommended courses of action to enable the implementation of an intervention if such intervention is needed. Continuous updating of the information display will allow a user to identify and assess the seriousness of a change in reported information. Accordingly, errors from missing important data or acting improperly with respect to deviations in reported data from a predetermined norm or a data anomaly will be substantially reduced.

An example of a still more advanced embodiment would be where the data sets within a number of circles are superimposed circles. The data anomalies would be evident for a single data set (a single patient) within a data universe (the patient data for a single practitioner or even a group of practitioners). This would allow a practitioner to immediately see, from his entire practice the data with critical abnormalities requiring immediate attention.

A yet still more advanced embodiment would be where a data universe would be rendered as a co-ordinate on a circle representing n-dimensions of data. This could be visualized by "cutting" the circle and collapsing the resulting line segment at a co-ordinate of a circle representing n-dimensions of data. The image at the co-ordinate would preserve all the upward or downward anomalies present on the entire original circle.

According to the present invention and further iterations, thereof, the set of extreme anomalies from infinitely complex data sets can be localized on a single display, such as a circle.

While the foregoing invention has been described according to its basic and advanced embodiments, those of ordinary skill in the art will understand that numerous other embodiments have been enabled by the foregoing disclosure. Such other embodiments shall fall within the scope and meaning of the appended claims.

I claim:

1. A system for display and prioritization of aggregated data comprising:
    a computer-enabled display comprising first:
        a geometric form, the geometric form representing the aggregated data in predetermined categories at fixed locations on the geometric form; and
        a visual display that represents separately data deviating from a non-critical range, wherein the data deviating from the non-critical range is represented above or below the geometric form at the fixed location for the predetermined category on the geometric form;
        wherein, when a plurality of sets of aggregated data or geometric forms is stacked or overlaid, the data is represented in the visual display as viewable from a top of a stack, and the data deviating from the non-critical range is immediately displayed and reviewed on a secondary screen when selected by a user;
        wherein the geometric form is a substantially circular form; and
        wherein a segment of an area within the substantially circular form forms a link to the secondary screen.

2. The system as defined in claim 1, wherein data falling within the non-critical range represents a normal condition or a non-critical abnormal condition and the data deviating from the non-critical range represents a critical abnormal condition.

3. The system as defined in claim 1, wherein each visual display representing data deviating from the non-critical range is represented by a substantially radial line segment extending substantially radially outwardly or inwardly from the substantially circular form.

13

4. A method for display and prioritization of aggregated data comprising the step of:
- a computer enabling a display depicting first a geometric form, the geometric form representing the aggregated data in predetermined categories at fixed locations on the geometric form, wherein the display represents separately data deviating from a non-critical range, wherein the data deviating from the non-critical range is represented above or below the geometric form at the fixed location for the predetermined category on the geometric form;
- wherein, when a plurality of sets of aggregated data or geometric forms is stacked or overlaid, the data is represented in the visual display as viewable from a top of a stack, and the data deviating from the non-critical range is immediately displayed and reviewed on a secondary screen when selected by the user;
- wherein the geometric form is a substantially circular form; and
- wherein a segment of an area within the substantially circular form forms a link to the secondary screen.

5. The method as defined in claim 4, wherein data falling within the non-critical range represents a normal condition or a non-critical abnormal condition and the data deviating from the non-critical range represents a critical abnormal condition.

6. The method as defined in claim 4, wherein each visual display representing data deviating from the non-critical range is indicated by a line segment extending substantially radially outwardly or inwardly from the substantially circular form.

7. A system for consistently identifying and assessing the severity of a health condition of a patient comprising:
- a computer-enabled display comprising first:
  - a geometric form, the geometric form representing aggregated data describing the health condition of the patient in predetermined categories at fixed locations on the geometric form; and
  - a visual display that represents separately data describing the health condition of the patient deviating from a non-critical range, wherein the describing the health condition of the patient deviating from the non-critical range is represented above or below the geometric form at the fixed location for the predetermined category on the geometric form;
- wherein the data describing the health condition of the patient deviating from the non-critical range is immediately displayed and reviewed on a secondary screen when selected by a user;
- wherein the geometric form is a substantially circular form; and
- wherein a segment of an area within the substantially circular form forms a link to the secondary screen.

8. The system as defined in claim 7, wherein data describing the health condition of the patient falling within the non-critical range represents a normal condition or a non-critical abnormal condition and the data describing the health condition of the patient deviating from the non-critical range represents a critical abnormal condition.

9. The system as defined in claim 7, wherein each visual display representing data describing the health condition of the patient deviating from the non-critical range is represented by a line segment extending substantially radially outwardly or inwardly from the substantially circular form.

10. A method for consistently identifying and assessing the seriousness of a health condition of a patient comprising the step of:
- a computer enabling a display depicting first a geometric form, the geometric form representing aggregated data describing the health condition of the patient in predetermined categories at fixed locations on the geometric form, wherein the display represents separately data describing the health condition of the patient deviating from a non-critical range, wherein the data describing the health condition of the patient deviating from the non-critical range is represented above or below the geometric form at the fixed location for the predetermined category on the geometric form;
- wherein the data describing the health condition of the patient deviating from the non-critical range is immediately displayed and reviewed on a secondary screen when selected by a user;
- wherein the geometric form is a substantially circular form; and
- wherein a segment of an area within the substantially circular form forms a link to the secondary screen.

11. The method as defined in claim 10, wherein data describing the health condition of the patient falling within the non-critical range represents a normal health condition or a non-critical abnormal condition and the data describing the health condition of the patient deviating from the non-critical range represents a critical abnormal condition.

12. The method as defined in claim 10, wherein each visual display representing data describing the health condition of the patient deviating from the non-critical range is represented by a line segment extending substantially radially outwardly or inwardly from the substantially circular form.

13. A method for providing information to a professional to assist the professional in making a judgment about a situation, the method comprising the step of:
- a computer enabling a display depicting first a geometric form, the geometric form representing aggregated data related to the situation in predetermined categories at fixed locations on the geometric form, wherein the display represents separately data related to the situation deviating from a non-critical range, wherein the data related to the situation deviating from the non-critical range is represented above or below the geometric form;
- wherein, when a plurality of sets of aggregated data related to the situation or geometric forms is stacked or overlaid, the data is represented in the visual display as viewable from a top of a stack, and the data related to the situation deviating from the non-critical range is immediately displayed and reviewed on a secondary screen of additional data when selected by the professional;
- wherein the geometric form is a substantially circular form; and
- wherein a segment of an area within the substantially circular form forms a link to the secondary screen.

14. The method as defined in claim 13, wherein data related to the situation falling within the non-critical range represents a normal condition or a non-critical abnormal condition and the data related to the situation deviating from the non-critical range represents a critical abnormal condition.

15. The method as defined in claim 13, wherein each visual display representing data related to the situation deviating from the non-critical range is represented by a substantially radial line segment extending substantially radially outwardly or inward from the substantially circular form.

16. A system for assisting a professional with display and prioritization of aggregated data for the purpose of rendering a professional judgment, the system comprising:
- a computer-enabled display comprising first:

a geometric form, the geometric form representing the aggregated data in predetermined categories at fixed locations on the geometric form; and a visual display that represents separately data deviating from a non-critical range, wherein the data deviating from the non-critical range is represented above or below the geometric form at the fixed location for the predetermined category on the geometric form;

wherein, when a plurality of sets of aggregated data or geometric forms is stacked or overlaid, the data is represented in the visual display as viewable from a top of a stack, and the data deviating from the non-critical range is immediately displayed and reviewed on a secondary screen when selected by the professional;

wherein the geometric form is a substantially circular form; and wherein a segment of an area within the substantially circular form forms a link to the secondary screen.

17. The system as defined in claim 16, wherein the computer-enabled display comprises removable labels describing the predetermined categories.

18. The system as defined in claim 16, wherein the computer-enabled display comprises an indicator for the professional to verify review of the data.

19. The system as defined in claim 16, wherein data falling within the non-critical range represents a normal condition or a non-critical abnormal condition and the data deviating from the non-critical range represents a critical abnormal condition.

20. The system as defined in claim 7, wherein, when a plurality of sets of aggregated data or geometric forms is stacked or overlaid, the data is represented in the visual display as viewable from a top of a stack.

21. The method as defined in claim 10, wherein, when a plurality of sets of aggregated data or geometric forms is stacked or overlaid, the data is represented in the visual display as viewable from a top of a stack.

* * * * *

UNITED STATES PATENT AND TRADEMARK OFFICE
CERTIFICATE OF CORRECTION

| | |
|---|---|
| PATENT NO. | : 8,489,544 B2 |
| APPLICATION NO. | : 12/156723 |
| DATED | : July 16, 2013 |
| INVENTOR(S) | : John P. Ford |

It is certified that error appears in the above-identified patent and that said Letters Patent is hereby corrected as shown below:

In the Claims:

Claim 7 (Column 13, line 41): replace "wherein the describing" with "wherein the data describing"

Claim 15 (Column 14, lines 62-63): replace "radially outwardly or inward" with "radially outwardly or inwardly"

Signed and Sealed this
Third Day of September, 2013

Teresa Stanek Rea
*Acting Director of the United States Patent and Trademark Office*